(12) United States Patent
Nearing et al.

(10) Patent No.: US 9,060,699 B2
(45) Date of Patent: Jun. 23, 2015

(54) MULTILEAD ECG TEMPLATE-DERIVED RESIDUA FOR ARRHYTHMIA RISK ASSESSMENT

(71) Applicant: Beth Israel Deaconess Medical Center, Inc., Boston, MA (US)

(72) Inventors: Bruce D. Nearing, North Reading, MA (US); Richard L. Verrier, Wellesley Hills, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 15 days.

(21) Appl. No.: 13/624,544

(22) Filed: Sep. 21, 2012

(65) Prior Publication Data
US 2014/0088449 A1   Mar. 27, 2014

(51) Int. Cl.
A61B 5/0452   (2006.01)
A61B 5/04   (2006.01)
A61B 5/0472   (2006.01)
(Continued)

(52) U.S. Cl.
CPC .......... *A61B 5/04012* (2013.01); *A61B 5/0452* (2013.01); *A61B 5/0456* (2013.01); *A61B 5/0472* (2013.01); *A61B 5/7246* (2013.01); *A61B 5/04525* (2013.01); *A61B 5/7275* (2013.01); *A61B 5/7278* (2013.01)

(58) Field of Classification Search
CPC .. A61B 5/0452; A61B 5/0464; A61B 5/0468; A61B 5/0472
USPC ........................................................ 600/516
See application file for complete search history.

(56) References Cited

U.S. PATENT DOCUMENTS 5,560,370 A * 10/1996 Verrier et al. ................. 600/518
5,921,940 A * 7/1999 Verrier et al. ................. 600/518
6,035,231 A * 3/2000 Sornmo et al. ................ 600/509
(Continued)

FOREIGN PATENT DOCUMENTS

WO   WO 2008/008361 A2   1/2008

OTHER PUBLICATIONS

Nearing, Bruce D. et al. "Cresendo in Depolarization and Repolarization Heterogeneity Heralds Development of Ventricular Tachycardia in Hospitalized Patients With Decompensated Heart Failure." *Circ Arrhythin Elecrophysiol*, vol. 5, pp. 84-90, Dec. 8, 2011.
(Continued)

*Primary Examiner* — Christopher D Koharski
*Assistant Examiner* — Jeremiah Kimball
(74) *Attorney, Agent, or Firm* — Sterne, Kessler, Goldstein & Fox P.L.L.C.

(57) ABSTRACT

A method and system for predicting the onset of heart arrhythmias more accurately observes trends in abnormal or pathologic morphology of the electrocardiogram (ECG). A first set of ECG signals is monitored from a patient. A baseline measurement is generated from the monitored first set of ECG signals to contain nonpathologic ECG morphologies in each lead. A second set of ECG signals is monitored from the patient and the baseline measurement is subtracted from the second set of ECG signals on a beat-to-beat basis. Afterwards, a residuum signal is generated for each lead based on the subtraction. R-wave heterogeneity, T-wave heterogeneity, P-wave heterogeneity, or ST-segment heterogeneity or other indicators of arrhythmia risk or myocardial ischemia are quantified based on the generated residuum signals.

25 Claims, 9 Drawing Sheets

(51) Int. Cl.
*A61B 5/00* (2006.01)
*A61B 5/0456* (2006.01)

(56) References Cited

U.S. PATENT DOCUMENTS

| | | | | |
|---|---|---|---|---|
| 6,169,919 | B1 * | 1/2001 | Nearing et al. | 600/518 |
| 6,178,347 | B1 * | 1/2001 | Olsson | 600/518 |
| 7,174,204 | B2 * | 2/2007 | Hadley et al. | 600/515 |
| 2002/0120206 | A1 * | 8/2002 | Taha et al. | 600/515 |
| 2002/0138013 | A1 * | 9/2002 | Guerrero et al. | 600/509 |
| 2002/0143265 | A1 * | 10/2002 | Ackerman et al. | 600/515 |
| 2002/0183639 | A1 | 12/2002 | Sweeney et al. | |
| 2005/0010122 | A1 * | 1/2005 | Nearing et al. | 600/509 |
| 2007/0010752 | A1 * | 1/2007 | Korhonen | 600/516 |
| 2007/0088395 | A1 * | 4/2007 | Province et al. | 607/5 |
| 2009/0281440 | A1 * | 11/2009 | Farazi et al. | 600/510 |

OTHER PUBLICATIONS

Acar, B., et al., "Spatial, temporal and wavefront direction characteristics of 12-lead T-wave morphology," *Medical & Biological Engineering & Computing 37(5)*:574-584, Springer, Germany (1999).

Bonizzi, P., et al., "Noninvasive Assessment of the Complexity and Stationarity of the Atrial Wavefront Patterns During Atrial Fibrillation," *IEEE Transactions on Biomedical Engineering 57(9)*: 2147-2157, IEEE Service Center, United States (2010).

Legarreta, I.R., et al., "Common spatial pattern: An improved method for atrial fibrillation wave extraction," *Computers in Cardiology 2007*:501-504, IEEE, United States (2007).

Malik, M., et al., "QT Dispersion Does Not Represent Electrocardiographic Interlead Heterogeneity of Ventricular Repolarization," *Journal of Cardiovascular Electrophysiology 11(8)*:835-843 (2000).

Markus, Z., et al., "Analysis of T-Wave Morphology From the 12-lead Electrocardiogarm for Prediction of Long-Term Prognosis in male US veterans," *Circulation 105(9)*:1066-1070, Lippincot Williams and Wilkins, United States (2002).

Nearing, B.D., et al., "Modified moving average analysis of T-wave alternans to predict ventricular fibrillation with high accuracy," *Journal of Applied Physiology 92(2)*:541-549, American Physiological Society, United States (2002).

Nearing, B.D., "Tracking cardiac electrical instability by computing interlead heterogeneity of T-wave morphology," *Journal of Applied Physiology 95(6)*:2265-2272, American Physiological Society, United States (2003).

Pueyo, E., et al., "Cardiac repolarization analysis using the surface electrocardiogram," *Philosophical Transactions of the Royal Society A 367*, 213-233 (2009).

International Search Report for International application No. PCT/US2013/060982, European Patent Office, Netherlands, mailed Aug. 1, 2014.

* cited by examiner

MULTILEAD ECG TEMPLATE-DERIVED RESIDUA FOR ARRHYTHMIA RISK ASSESSMENT

STATEMENT REGARDING FEDERALLY-SPONSORED RESEARCH AND DEVELOPMENT

The U.S. government has a paid-up license in this invention and the right in limited circumstances to require the patent owner to license others on reasonable terms as provided for by the terms of grant R21 HL085720 awarded by National Institutes of Health (NIH).

Part of the work performed during development of this invention utilized U.S. Government funds. The U.S. Government has certain rights in this invention.

BACKGROUND OF THE INVENTION

1. Field of the Invention

Embodiments herein relate to systems and methods for determining potential health risks by analyzing electrocardiograms (ECG).

2. Background Art

Heart rhythm abnormalities, referred to as "arrhythmias" and originating from both the atria and ventricles, constitute a predisposing condition leading to significant morbidity and mortality in the U.S. population. Atrial fibrillation affects 2.2 million U.S. citizens and accounts for 500,000 hospitalizations annually. Sudden cardiac death due to ventricular arrhythmias accounts for 310,000 U.S. deaths each year. Thus, there is a great need to improve arrhythmia risk assessment, which can lead to better diagnosis of underlying disease and help to guide therapy.

The public health impact of arrhythmias is underscored by the prevalence of heart failure. This condition in which atrial and ventricular arrhythmias co-exist affects over five million Americans, with hospitalization of more than one million patients for decompensated heart failure yearly. These individuals experience a high degree of ventricular ectopy and spontaneous ventricular arrhythmias. Sudden cardiac death constitutes a high proportion of deaths in the heart failure population (58% in New York Heart Association [NYHA] class III and 33% in NYHA class IV). However, no standard electrocardiographic markers, including ventricular ectopy or arrhythmias, have proven to be reliable indicators of life-threatening cardiac arrhythmias.

Considerable evidence indicates that analysis of subtle variations in ECG signal morphology, including T-wave heterogeneity, T-wave variability, and T-wave alternans (TWA) may reveal arrhythmia risk. However, intrinsic morphology differences among ECG signals in the standard leads may mask arrhythmogenic ECG morphology changes. Complex influences including impedance and ECG vector cancellation of electrocardiographic signals contribute to differences in the projected amplitude of the signals to the body surface. Thus, microvolt levels of ECG morphology changes that are associated with disease states such as ischemic episodes, acute coronary syndrome, or heart failure may be difficult and imprecise to detect.

BRIEF SUMMARY OF THE INVENTION

Example methods and systems are described herein for embodying an approach to isolating abnormal ECG signals to capture and measure morphologic ECG changes that may be associated with lethal cardiac arrhythmias.

In an embodiment, an example method is described. The method includes receiving a first set of electrocardiogram (ECG) signals from spatially separated leads. The method generates a baseline beat template associated with the morphology of each ECG signal of the first set of ECG signals. The method includes receiving a second set of ECG signals from spatially separated leads and calculating, for each lead, a difference between each ECG signal in the second set of ECG signals and the corresponding baseline beat template to produce a residuum signal for each lead. The method then includes quantifying ECG characteristics based on the residuum signals, wherein the characteristics are associated with arrhythmia risk. R-wave heterogeneity and/or T-wave heterogeneity may be quantified based on the generated residuum signals. The residuum signals may also be used to quantify P-wave changes indicative of risk of atrial arrhythmias or ST-segment changes among spatially separated leads to identify regions of myocardial ischemia.

In another embodiment, an electrocardiogram system is described. The system includes an input module and a processor. The input module receives ECG signals from spatially separated leads. The processor is designed to generate a baseline beat template associated with the morphology of each ECG signal of a first set of ECG signals from the spatially separated leads. The processor further calculates a difference between each ECG signal of a second set of ECG signals from the spatially separated leads and the corresponding baseline beat template to produce a residuum signal for each of the spatially separated leads. The processor is also configured to quantify ECG characteristics based on the residuum signals, wherein the characteristics are associated with arrhythmia risk. The characteristics include, for example, R-wave heterogeneity, T-wave heterogeneity, P-wave heterogeneity and/or ST-segment heterogeneity.

In another embodiment, a computer program product stored on a computer readable media includes a set of instructions that, when executed by a computer device, perform the steps of the above described method.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant arts) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the present invention and to enable a person skilled in the relevant art(s) to make and use the present invention.

Figure 1:
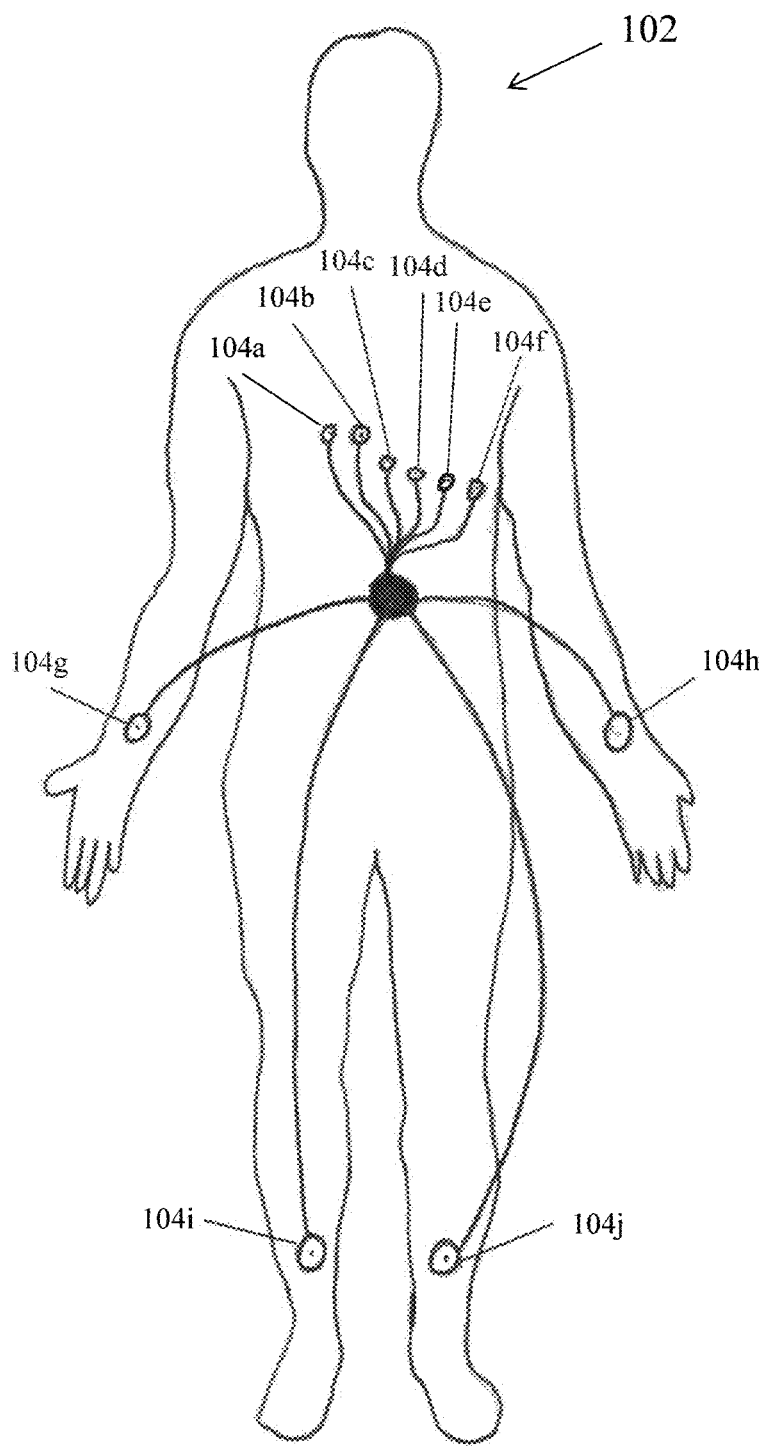
FIG. 1 illustrates leads of an ECG device placed on a patient, according to an embodiment.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

This specification discloses one or more embodiments that incorporate the features of this invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 illustrates a patient 102 that is attached to various leads of an ECG recording device, according to an embodiment. The leads may be used to monitor a standard 12-lead ECG. In this example, six leads (leads 104a-f) may be placed across the chest of patient 102 while four other leads (leads 104g-j) are placed with two near the wrists and two near the ankles of patient 102.

It should be understood that the exact placement of the leads is not intended to be limiting. For example, the two lower leads 104i and 104j may be placed higher on the body, such as on the outer thighs. In another example, leads 104g and 104h are placed closer to the shoulders while leads 104i and 104j are placed closer to the hips of patient 102. In still other examples, not all ten leads are required to be used in order to monitor ECG signals from patient 102.

In an embodiment, signals are monitored from each of leads 104a-j during a standard 12-lead ECG recording. The resulting ECG signal may be analyzed over time to determine various health factors such as heart rate, strength of heart beat, and any indicators of abnormalities. However, changes in the various signals received amongst leads 104a-j may be very small and difficult to detect. Any trend in the changing signal amplitude for certain areas of the ECG morphology could be vital in predicting the onset of potentially fatal heart complications. For example, prediction of heart arrhythmias may be possible by observing trends in the R-wave heterogeneity, T-wave heterogeneity, P-wave heterogeneity and/or T-wave alternans from the monitored ECG signals. The observation of using T-wave alternans as predictors for heart arrhythmias has been discussed previously in U.S. Pat. No. 5,560,370, the disclosure of which is incorporated by reference herein in its entirety. Spatial differences in ST-segment morphology, termed ST-segment heterogeneity, may provide evidence of regionality of myocardial ischemia, a characteristic that contributes to risk for lethal arrhythmia.

The challenge is to separate these biologically significant microvolt-level changes from the intrinsic differences in ECG morphology. In an embodiment, the technique employed herein utilizes a multi-lead ECG median-beat baseline for each lead, which allows for the determination of ECG residua by subtraction of the baseline from the collected ECG signals. These residua may be evaluated in association with R-wave and T-wave heterogeneity analysis and other parameters for heart arrhythmia prediction and/or for myocardial ischemia assessment. Ultimately, the implementation of embodiments described herein can lead to improved identification of individuals at risk for lethal cardiac arrhythmias and to a reduction in cases of sudden cardiac death.

Figure 2:
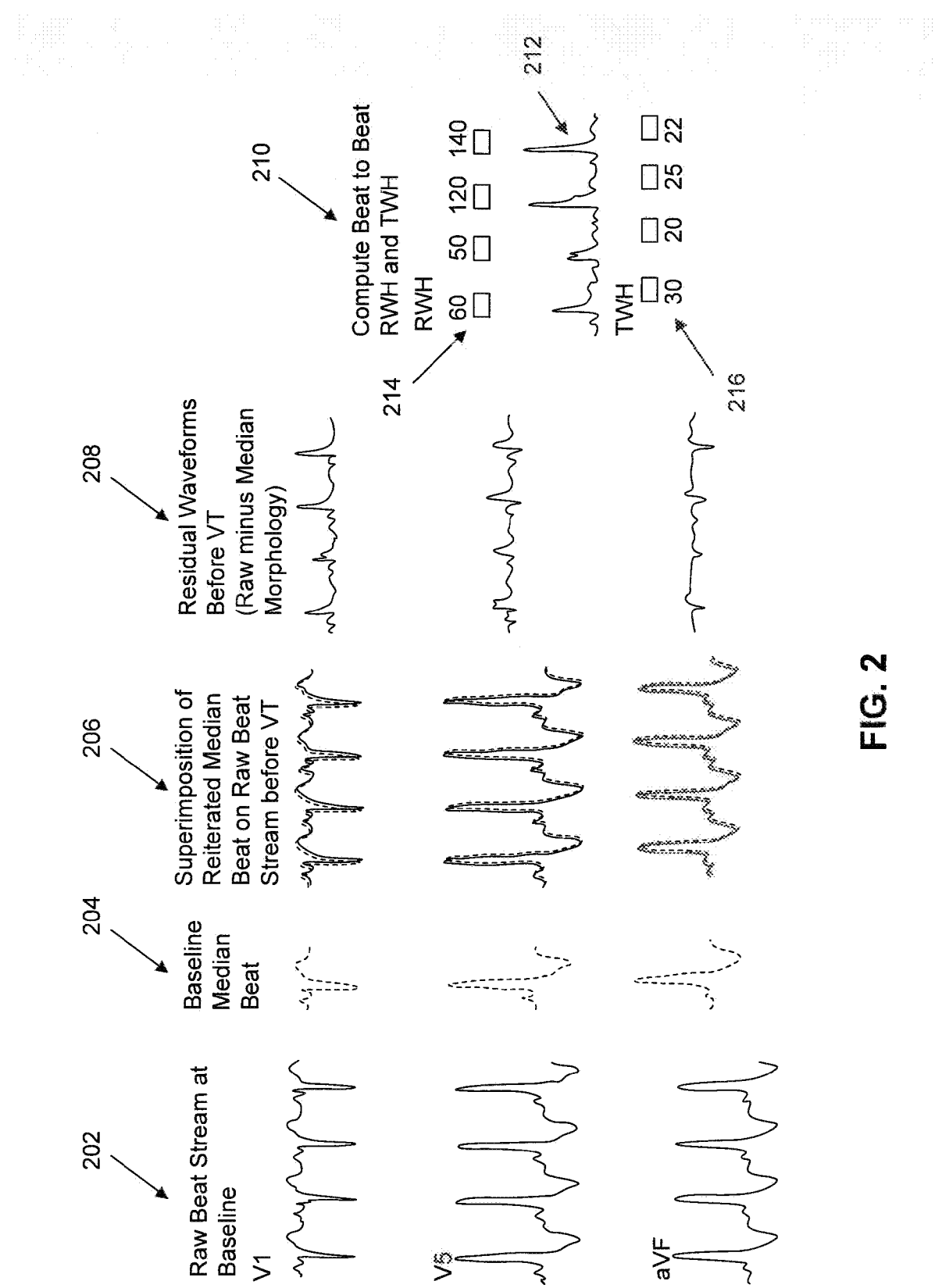
FIG. 2 illustrates signal processing techniques of an ECG signal, according to an embodiment.

FIG. 2 illustrates a signal processing procedure for generating ECG residua and detecting changes, for example, in R-wave and T-wave heterogeneity from the signals received from various leads, according to an embodiment. For simplicity, the signal processing procedure described with reference to FIG. 2 will be referred to herein as the multi-lead residuum procedure. In one example, signals from three different ECG leads (V1, V5, and aVF) are shown in column 202. The ECG signals to be analyzed in accordance with the present disclosure may be sensed in real-time from a patient and processed on a real-time or near real-time basis (e.g., within seconds or minutes of being collected from a patient). Alternatively, the ECG signals may be received from some storage medium (e.g., an analog or digital storage device) for analysis in accordance with the present disclosure.

A baseline recording 202 is generated from the signals received from each of the ECG leads, according to an embodiment. In one example, the baseline measurement is generated by computing a median-beat 204 $B_{i,n}(t)$ for n=1 . . . N beats is generated from the collected signals shown in column 202, and ECG signals, where M=all ECG leads. An example calculation of the median-beat is shown below in equation 1.

$$B_{i,n}(t) = B_{i,n-1}(t) + \Delta_{i,n} \quad (1)$$

$\Delta_{i,n} = -32$ if $\delta \leq -32$ $\Delta_{i,n} = \delta$ if $-1 \geq \delta \geq -32$ $\Delta_{i,n} = -1$ if $0 \geq \delta \geq -1$ $\Delta_{i,n} = 0$ if $\delta \leq -0$ $\Delta_{i,n} = 1$ if $1 \geq \delta \geq -0$ $\Delta_{i,n} = \delta$ if $0 \geq \delta \geq 1$ $\Delta_{i,n} = 32$ if $\delta \leq -32$ where $\delta = (ECG_{i,n-1}(t) - B_{i,n-1}(t))/8$ and $B_{i,0}(t) = ECG_{i,0}(t)$ i=1 ... M EGG signals n=1 ... N Baseline Beats In an embodiment, the sequence starts with the first beat, and each successive beat then contributes a limited amount to the median-beat computation in each ECG lead. The baseline measurement contains nonpathologic morphologies in each ECG lead and may be associated with a period of quiet rest when morphology differences over time are at a minimum. This baseline measurement may be calculated by computing the median beat 204 over a time period between, for example, 5 and 10 minutes. Collection times over 10 minutes may be used as well, but would typically not be necessary for calculating a stable baseline signal. Alternatives to the use of median beats include calculating the baseline signal from an average of all the beats in the baseline time period or using a single, representative beat from the baseline time period as the baseline signal. These methods are simpler but not as robust as median beat calculation. Baseline measurements of the ECG signals received via leads V1, V5, and aVF are shown in column 204.

Once the baseline measurement 204 has been generated, a second set of ECG recordings, $ECG_i(t)$, is made. In an embodiment, the second set of ECG recordings is made soon after (e.g., immediately after) the baseline recording. However, it is also possible that the second set of ECG recordings is made at any period of time after the baseline recording has been generated. For example, the baseline recording for a particular patient may be saved and used a year later when that patient returns to have a second set of ECG recordings made. It should also be understood that there is no restriction as to the duration of the second set of ECG recordings.

In an embodiment, the baseline measurement $B_{i,N}(t)$ is reiterated and subtracted on a beat-to-beat basis from the second set of ECG recordings $ECG_i(t)$ for each lead. Each baseline measurement beat may be lined up either temporally or spatially with the various beats from each collected signal for each lead in order to subtract the morphologies from one another. Column 206 illustrates the superposition of the baseline measurement 204 $B_{i,N}(t)$ over the second set of ECG recordings $ECG_i(t)$ in order to subtract the baseline signal.

The residuum signal resulting from the subtraction for each lead is illustrated in column 208, according to an embodiment. Likewise, equation 2 below provides the generation of the residuum signal $e_i(t)$.

$$e_i(t) = ECG_i(t) - B_N(t) \quad (2)$$

i=1 ... M ECG signals)

N=Number of beats in baseline sequence

Once the residuum signals have been calculated for each lead, they may be used for calculating the R-wave heterogeneity (RWH) and T-wave heterogeneity (TWH), according to an embodiment. By observing trends in the RWH and/or TWH, cardiac events such as ventricular tachycardia may be predicted well in advance, allowing for preventive procedures to be taken. The RWH and TWH may be calculated by first averaging the spatio-temporal signals of each of the residuum signals to generate an averaged residuum signal as shown below in equation 3.

$$\overline{e(t)} = \frac{1}{M} \sum_{i=1}^{M} e_i(t) \quad (3)$$

In the above equation, and for other equations used herein, M is an integer greater than two and equal to the number of total ECG signals collected. In one example, one ECG signal is recorded from each lead of the standard 12-lead ECG.

Next, in an embodiment, a second central moment 212 about the averaged residuum signal is determined by taking the mean-square deviation of the various ECG signals about the average signal. This step is shown below in Equation 4.

$$\mu_2(t) = \frac{1}{M} \sum_{i=1}^{M} (e_i(t) - \overline{e(t)})^2 \quad (4)$$

With the second central moment 212 calculated, RWH 214 may be determined as the maximum square root of the second central moment of the ECG residua occurring within the QRS segment. In an embodiment, the QRS segment begins at the Q-wave and ends at the J-point of a standard ECG signal. Equation 5 below provides an example calculation for the RWH.

$$RWH = \underset{Q-Waveonset \leq t \leq J-point}{MAX} \sqrt{\mu_2(t)} \quad (5)$$

TWH 216 may be determined as the maximum square root of the second central moment of the ECG residua occurring within the JT interval. The JT interval occurs approximately from 60 to 290 msec after the R-wave of a standard ECG signal. Equation 6 below provides an example calculation for the TWH.

$$TWH = \underset{J-point \leq t \leq T-waveend}{MAX} \sqrt{\mu_2(t)} \quad (6)$$

Computation of residuum signals may be also useful in calculating heterogeneity of the P-Wave (PWH) from its onset to offset, which relates to atrial arrhythmias, and heterogeneity of the ST-Segment (STWH) from the J-point to the onset of the T-wave, which identifies nonhomogeneous features of myocardial ischemia.

$$PWH = \underset{P-Waveonset \leq t \leq P-Waveoffset}{MAX} \sqrt{\mu_2(t)} \quad (7)$$

$$STWH = \underset{J-point \leq t \leq T-Waveonset}{MAX} \sqrt{\mu_2(t)} \quad (8)$$

Column 210 illustrates results 212 of second central moment analysis of the residuum signals as well as the areas of the signal that correspond to RWH measurements 214 and TWH measurements 216, according to an embodiment. As shown in the example, the RWH and TWH measurements may change between beats. Peak levels of RWH and TWH are averaged for each 15-sec sampling period. Trends in the changing RWH and/or TWH may be used to identify short- or long-term risk for cardiac arrhythmias. In one example, the RWH and/or TWH may be reported over a given period of time for further analysis and/or data presentation.

Figure 3:
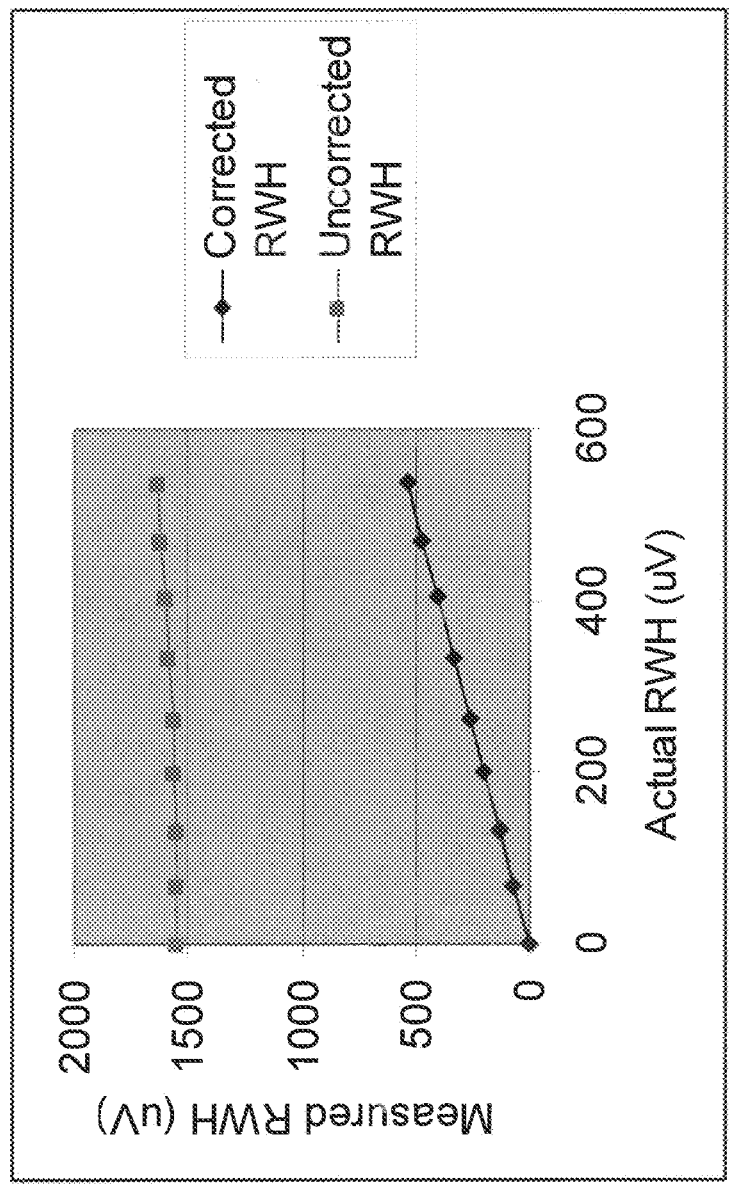
FIG. 3 illustrates results of calculating R-wave heterogeneity in simulated ECGs, according to an embodiment.

FIG. 3 illustrates results for measuring RWH in simulated ECG signals with various RWH levels. The ECG signals were generated using a C++ program with P-waves, R-waves, T-waves, and ST segments approximated by geometric shapes whose relative timing and amplitude were similar to surface ECGs. The results in FIG. 3 demonstrate that the measured RWH (y-axis) was highly correlated with the actual input RWH (x-axis) when corrected by using the multi-lead residuum procedure (diamonds). However, when uncorrected, the program was unable to determine accurately the RWH as shown by the uncorrected data points (squares), as results varied by up to 1500 microvolts from the input RWH signal.

Figure 4:
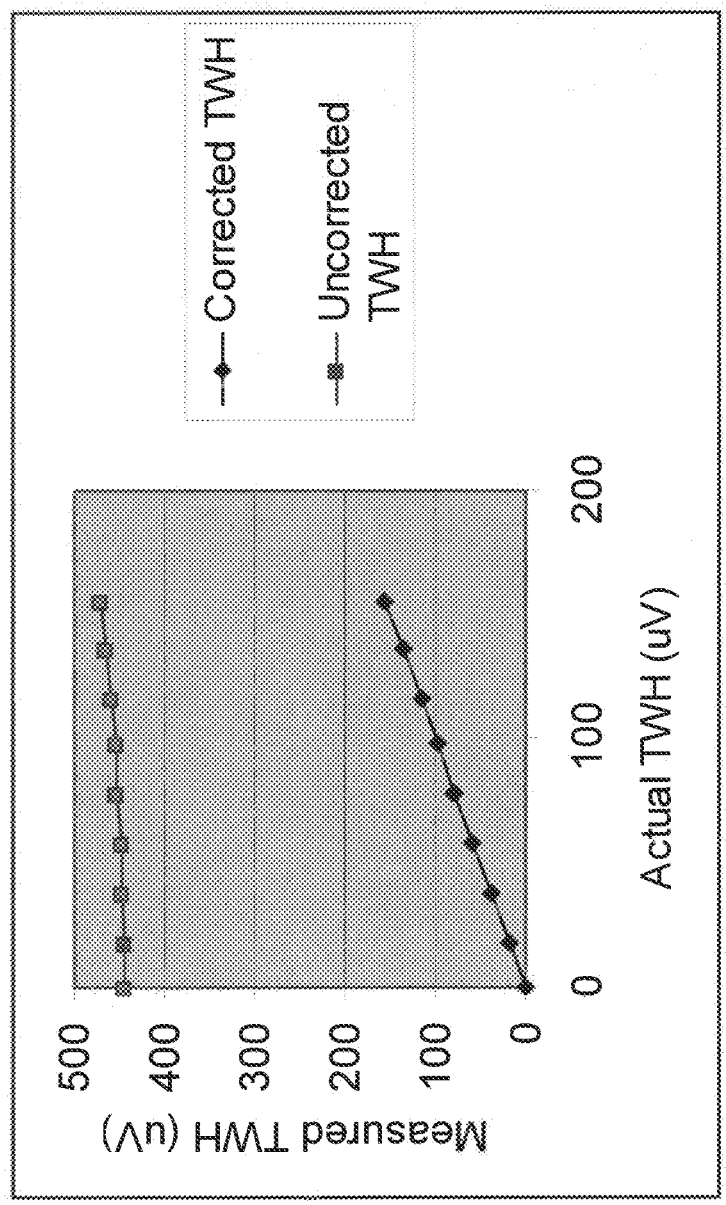
FIG. 4 illustrates results of calculating T-wave heterogeneity in simulated ECGs, according to an embodiment.

FIG. 4 illustrates results for measuring TWH in simulated ECG signals with various TWH levels. The ECG signals were generated using a C++ program with P-waves, R-waves, T-waves, and ST segments approximated by geometric shapes whose relative timing and amplitude were similar to surface ECGs. The results in FIG. 4 demonstrate that the measured TWH (y-axis) was highly correlated with the actual input TWH (x-axis) when corrected by using the multi-lead residuum procedure (diamonds). However, when uncorrected, the program was unable to determine accurately the TWH as shown by the uncorrected data points (squares), as results varied by up to 450 microvolts from the input TWH signal.

Thus, the RWH and TWH algorithm accurately tracked heterogeneities in R-wave and T-wave morphology in simulated ECGs when using the multi-lead residuum procedure but not in its absence. When calculating the residua, a linear relationship between the input and output values of RWH (range: 0-538 µV) and TWH (0-156 µV) estimated by second central moment analysis with a correlation coefficient of $r^2=0.999$ ($P<0.001$) was observed.

The embodied multi-lead residuum procedure for accurately determining RWH and TWH was validated via the simulation experiments shown in FIGS. 3 and 4. However, analysis of ECGs from a clinical trial was also conducted to demonstrate the capacity of the procedure to predict dangerous cardiac complications such as ventricular tachycardia.

The capacity of multi-lead ECG residua to predict ventricular arrhythmia was examined by comparing RWH and TWH output with and without calculation of the residua in clinical ambulatory ECG recordings obtained in hospitalized patients with non-sustained ventricular tachycardia. The PRECEDENT (Prospective Randomized Evaluation of Cardiac Ectopy with Dobutamine or Nesiritide Therapy) trial (www.clinicaltrials.org #NCT00270400) enrolled 255 patients aged ≥18 years with NYHA class III or IV congestive heart failure and symptomatic, decompensated congestive heart failure for which inpatient, single-agent, intravenous therapy with either nesiritide or dobutamine was deemed appropriate. All patients were monitored by ambulatory ECG recording for the 24-hour period immediately before the start of the study drug (pre-randomization ambulatory ECG tape).

Ambulatory ECGs recorded during the pre-randomization phase of the PRECEDENT trial were analyzed from all 22 patients who experienced a single bout of ventricular tachycardia (≥4 heats at heart rates of >100 beats/min) following 120 minutes of stable sinus rhythm and without atrial fibrillation. The Beth Israel Deaconess Medical Center Committee on Clinical Investigations certified the exempt status of this reanalysis of existing data from a completed clinical trial under exemption number 4 of the Code of Federal Regulations, 45 CFR 46.101(b).

The continuous ECGs were analyzed with and without correction by ECG residua in leads V1, V5, and aVF by subtracting the median-beat baseline ECG, which was generated from ECGs recorded during a quiescent period at 60 to 75 minutes before the arrhythmia occurred. Then, the ECG heterogeneity signal was computed from the ECG residua as the square root of the sum of the squares of the differences between the corrected signal and the mean of the corrected signals. RWH was calculated as the maximum value of the heterogeneity signal in the interval from the beginning of the Q wave to the end of the S wave. TWH was calculated as the maximum value of the heterogeneity signal in the interval between the J point and the end of the T wave. The analysis window began at 75 minutes before ventricular tachycardia. RWH and TWH maxima were computed for each 15-second interval, comparing signals in leads V1, V5, and aVF, and averaged over 15-minute epochs. Correlation coefficients of input-output relationships were calculated for input-output relationships by Pearson's coefficient. RWH and TWH levels at 45-60, 30-45, 15-30, and 0-15 minutes were compared with baseline at 60 to 75 minutes before the onset of the arrhythmia in PRECEDENT trial patients. ANOVA was used with Tukey test for multiple comparisons (*$p<0.05$).

Figure 5:
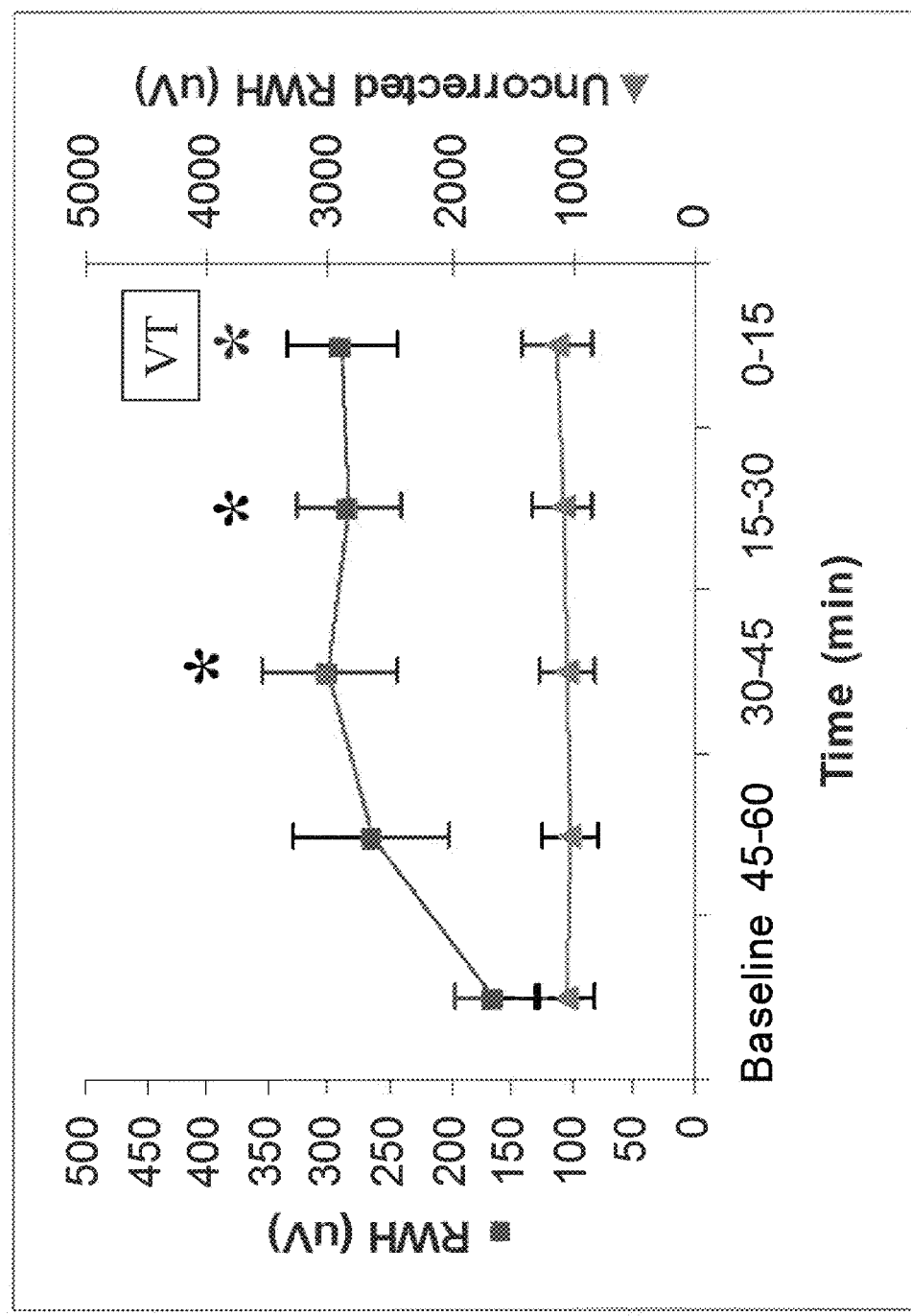
FIG. 5 illustrates results of measured R-wave heterogeneity before a ventricular tachycardia event, according to an embodiment.
Figure 6:
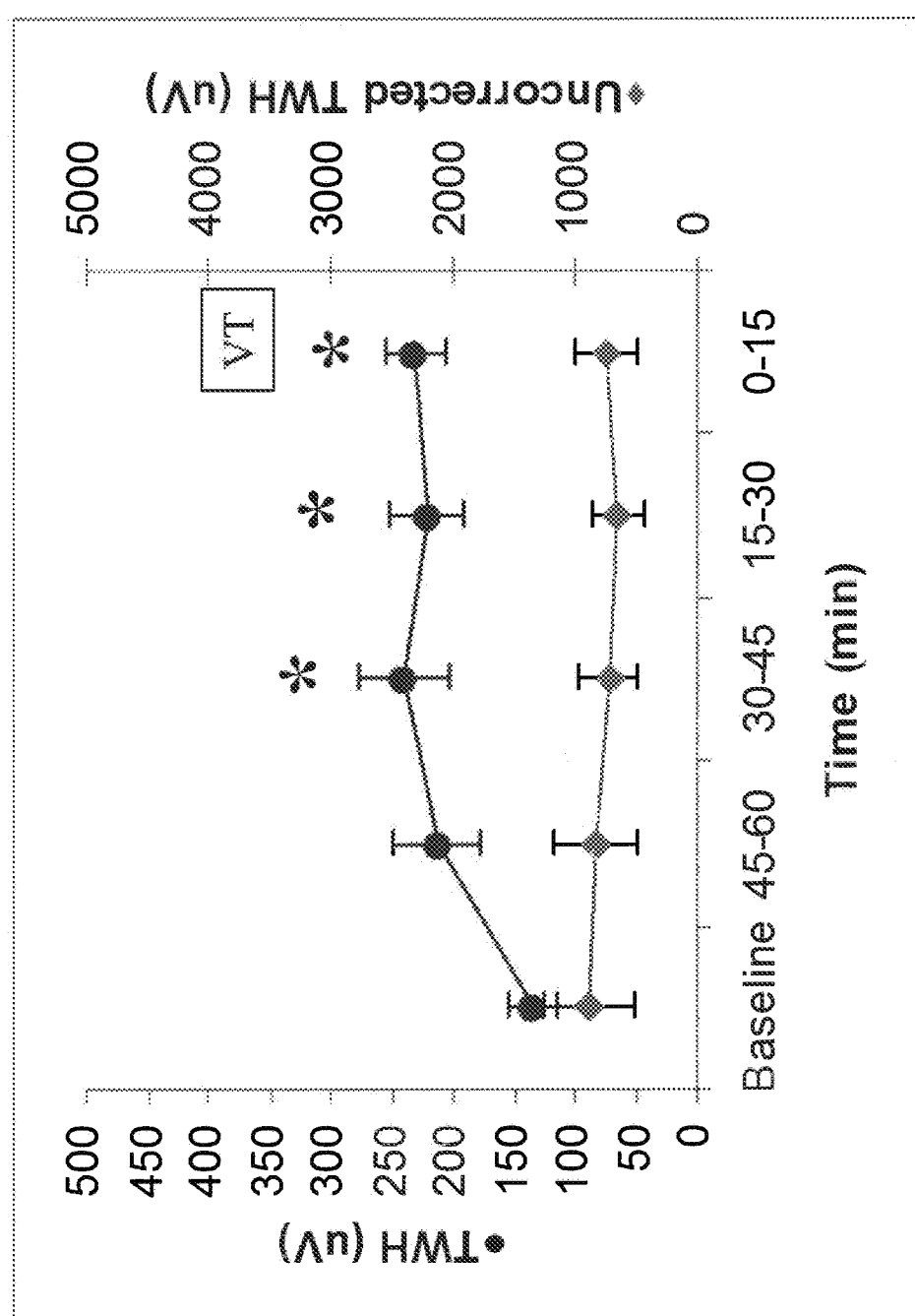
FIG. 6 illustrates results of measured T-wave heterogeneity before a ventricular tachycardia event, according to an embodiment.

FIGS. 5 and 6 illustrate the results for the RWH and TWH respectively obtained for those patients prior to ventricular tachycardia. A noticeable crescendo in RWH (FIG. 5) and TWH levels (FIG. 6) was observed prior to ventricular tachycardia when using the multi-lead residuum procedure (left y-axes). Maximum RWH across leads V1, V5, and aVF rose from 164.1±33.1 µV at baseline to 299.8±54.5 µV at 30 to 45 minutes before the arrhythmia ($P<0.05$). Meanwhile, maximum TWH across leads V1, V5, and aVF rose from 134.5±20.6 µV at baseline to 239.2±37.0 µV at 30 to 45 minutes before the arrhythmia ($p<0.05$). Just before ventricular tachycardia, maximum RWH and TWH levels remained elevated at 289.5±45.9 and 230.9±24.7 µV, respectively ($p<0.05$). Although the extent of change varied among patients, the crescendo pattern in ECG heterogeneity before non-sustained ventricular tachycardia was consistent (Pearson correlation coefficient comparing RWH and TWH, 0.51; $P=0.01$). In 20 of 22 (91%) patients, RWH or TWH remained elevated before onset of non-sustained ventricular tachycardia.

When R-wave and T-wave heterogeneity were calculated without employing the multi-lead residuum procedure, the levels of both RWH (FIG. 5) and TWH (FIG. 6) were high during the initial baseline period (right y-axes). The values were 1061.0±222.9 µV for RWH and 882.5±375.2 µV for TWH and were not statistically different at the time of onset of ventricular tachycardia.

Figure 7:
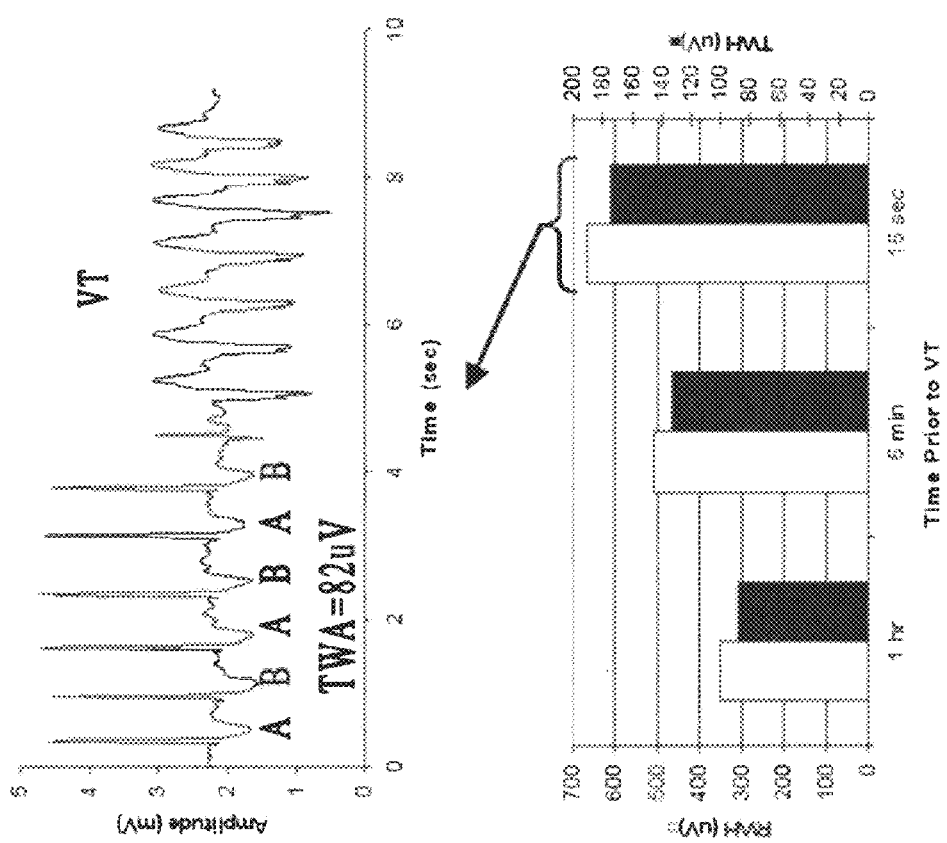
FIG. 7 illustrates results of measured R-wave and T-wave heterogeneity before a ventricular tachycardia event, according to an embodiment.

T-wave alternans (TWA) is another indicator of risk for lethal cardiac arrhythmias and can also be measured from the ECG along with the TWH measurements, according to an embodiment. FIG. 7 (lower panel) provides an example of the measured TWH (right y-axis) and RWH (left y-axis) of one patient at various times before the patient experienced ventricular tachycardia. Also illustrated is the measured TWA (~82 μV) (upper panel) during the time leading up to the ventricular tachycardia. This patient exhibited increased levels of RWH and TWH that heralded the onset of TWA and ventricular tachycardia.

Figure 8:
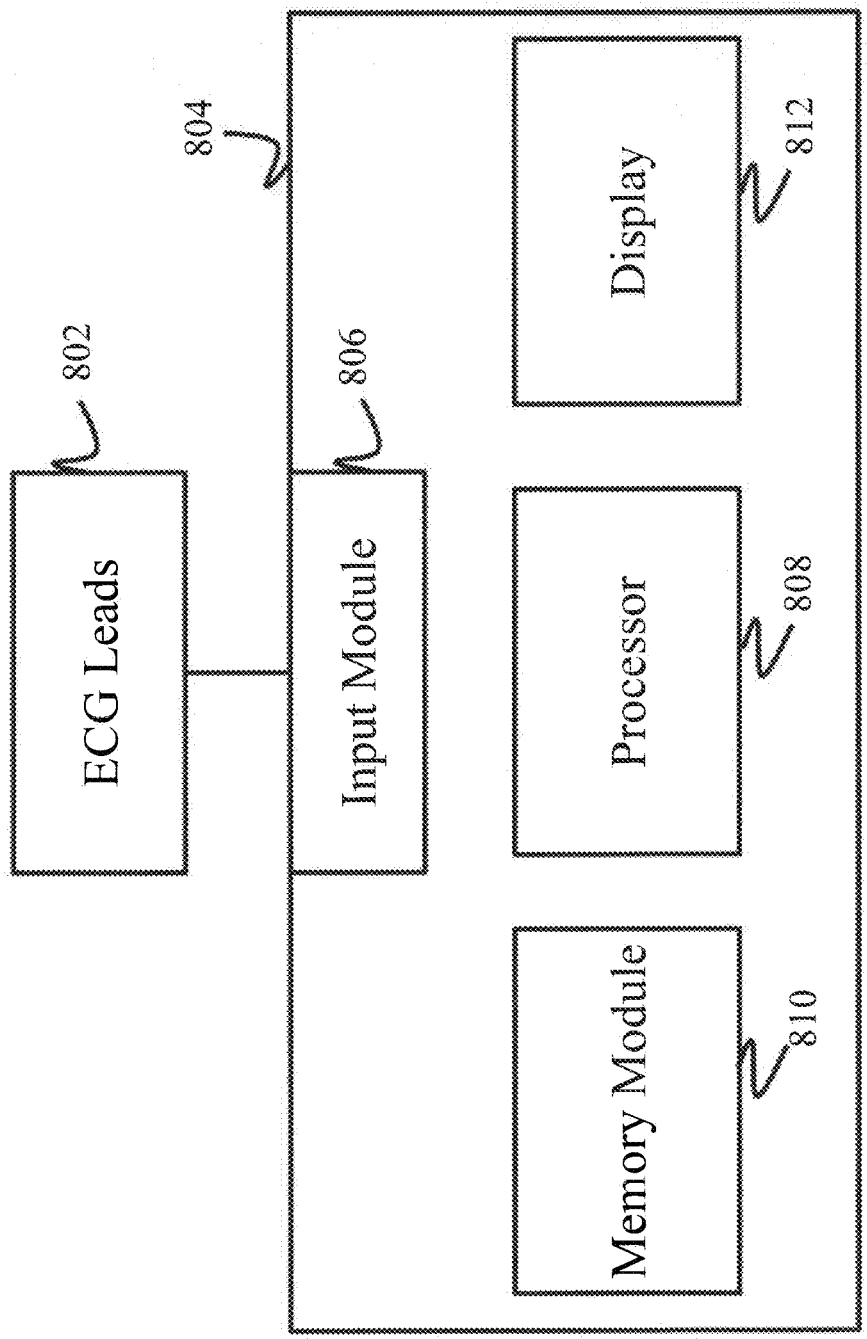
FIG. 8 illustrates an example ECG system, according to an embodiment.

FIG. 8 illustrates an example ECG system 800 configured to perform the embodied multi-lead residuum procedure. ECG system 800 may be used at a hospital or may be a portable device for use wherever the patient may be. In another example, ECG system 800 may be an implantable biomedical device with leads implanted in various locations around the body of a patient. ECG system 800 may be part of or may be coupled with other implantable biomedical devices such as a cardiac pacemaker, an implantable cardioverter-defibrillator (ICD) or a cardiac resynchronization therapy (CRT) device. In the case of ICD or CRT devices, analysis of the residuum signal will be analyzed after inverse filtering of the ECG signal to offset device-specific ECG filters and reconstruct the device output.

ECG system 800 includes leads 802 and a main unit 804. Leads 802 may comprise any number and type of electrical lead. For example, leads 802 may comprise ten leads to be used with a standard 12-lead ECG. Leads 802 may be similar to leads 104a-j as illustrated in FIG. 1 and described previously. In another example, leads 802 may comprise implanted electrical leads, such as insulated wires placed throughout the body.

Main unit 804 may include an input module 806, a processor 808, a memory module 810 and a display 812. Input module 806 includes suitable circuitry and hardware to receive the signals from leads 802. As such, input module 806 may include components such as, for example, analog-to-digital converters, de-serializers, filters, and amplifiers. These various components may be implemented to condition the received signals to a more suitable form for further signal processing to be performed by processor 808.

It should be understood that in the case of the embodiment where ECG system 800 is an implantable biomedical device, display 812 may be replaced with a transceiver module configured to send and receive signals such as radio frequency (RF), optical, inductively coupled, or magnetic signals. In one example, these signals may be received by an external display for providing visual data related to measurements performed by ECG system 800 and analysis performed after inverse filtering of the received signal to reconstruct the signal following filtering by the device.

Processor 808 may include one or more hardware microprocessor units. In an embodiment, processor 808 is configured to perform signal processing procedures on the signals received via input module 806. For example, processor 808 may perform the multi-lead residuum procedure as previously described for aiding in the prediction of heart arrhythmias. Processor 808 may also comprise a field-programmable gate array (FPGA) that includes configurable logic. The configurable logic may be programmed to perform the multi-lead residuum procedure using configuration code stored in memory module 810. Likewise, processor 808 may be programmed via instructions stored in memory module 810.

Memory module 810 may include any type of memory including random access memory (RAM), read-only memory (ROM), electrically-erasable programmable read-only memory (EEPROM), FLASH memory, etc. Furthermore, memory module 810 may include both volatile and non-volatile memory. For example, memory module 810 may contain a set of coded instructions in non-volatile memory for programming processor 808. The calculated baseline signal may also be stored in either the volatile or non-volatile memory depending on how long it is intended to be maintained. Memory module 810 may also be used to save data related to the calculated TWH or RWH, including trend data for each.

Figure 9:
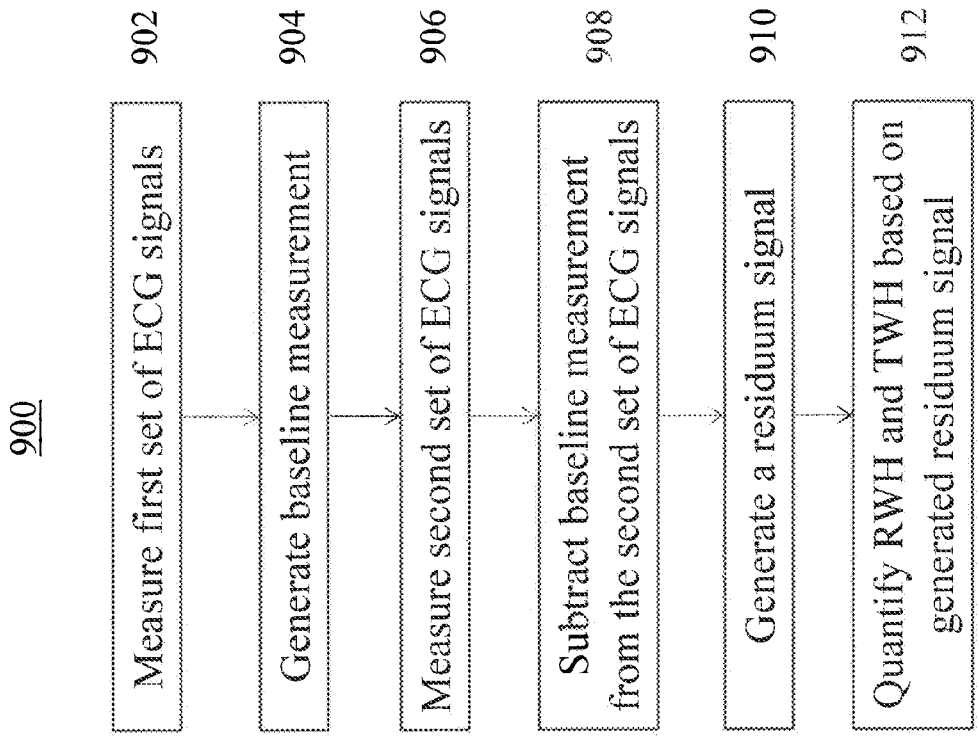
FIG. 9 illustrates an example method, according to an embodiment.

In an embodiment, main unit 804 includes display 812 for providing a visual representation of the received signals from leads 802. Display 812 may utilize any of a number of different display technologies such as, for example, liquid crystal display (LCD), light emitting diode (LED), plasma or cathode ray tube (CRT). An ECG signal from each of leads 802 may be displayed simultaneously on display 812. In another example, a user may select which ECG signals to display via a user interface associated with main unit 804. Display 812 may also be used to show data trends over time, such as displaying trends of the calculated RWH and TWH FIG. 9 illustrates a flowchart depicting a method 900 for predicting heart arrhythmias based on RWH and TWH, according to an embodiment. Method 900 may be performed by the various components of ECG system 800. It is to be appreciated that method 900 may not include all operations shown or perform the operations in the order shown.

Method 900 begins at step 902 where a first set of ECG signals is monitored from a patient. The signals may be monitored via leads such as those illustrated in FIG. 1, or via implantable leads.

At step 904, a baseline measurement associated with the morphology of the measured first set of ECG signals is generated. The baseline measurement may be generated by computing a median-beat sequence as described previously. The baseline measurement may be calculated over a period of 5 to 10 minutes in order to achieve a stable baseline signal. In an embodiment, a baseline measurement is generated for each lead of the standard 12-lead ECG.

At step 906, a second set of ECG signals is monitored from the patient. The second set of signals may be monitored directly after monitoring the first set of signals or at any time after monitoring the first set of signals.

At step 908, the baseline measurement is subtracted from the second set of monitored ECG signals. Each baseline measurement beat may be lined up either temporally or spatially with the various beats from each collected ECG signal for each lead in order to subtract the morphologies from one another. In an embodiment, step 908 is performed independently for each lead of the standard 12-lead ECG using the baseline signal generated for each associated lead.

At step 910, a residuum signal is generated for each lead based on the subtraction performed in step 908. The residuum signal may be used to identify microvolt-level signal changes in particular segments of the ECG signal that would be otherwise difficult to detect.

At step 912, RWH and TWH are quantified based on the generated residuum signals. In an embodiment, the residuum signals are calculated from each lead and the second central moment is derived for determining RWH and TWH.

Method 900 may be realized as a computer program product stored on a computer readable media. The computer program product includes a set of instructions that, when executed by a computing device, such as processor 808, perform the series of steps illustrated as part of method 900. Additionally, the instructions may include operations for measuring T-wave alternans (TWA), and determining trends of peak TWA, TWH and RWH values. The trends may be used to predict the onset of various heart arrhythmias, such as ventricular tachycardia.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of quantifying risk of cardiac arrhythmia, comprising:
   receiving a first set of electrocardiogram (ECG) signals from spatially separated leads;
   generating a baseline beat template associated with the morphology of each ECG signal of the first set of ECG signals;
   receiving a second set of ECG signals from spatially separated leads;
   calculating, for each lead, a difference between each ECG signal in the second set of ECG signals and the corresponding baseline beat template to produce a residuum signal for each lead;
   averaging the residuum signals across the leads to produce an averaged residuum signal; and
   quantifying a spatio-temporal heterogeneity of the second set of ECG signals based on the residuum signals and the averaged residuum signal, wherein the spatio-temporal heterogeneity is associated with arrhythmia risk.

2. The method of claim 1, wherein the quantifying step comprises:
   quantifying at least one of R-wave heterogeneity, T-wave heterogeneity, P-wave heterogeneity, and ST-segment heterogeneity.

3. The method of claim 2, wherein the first receiving step comprises monitoring ECG signals from a patient using a standard 12-lead ECG, wherein the generating step comprises generating a baseline measurement for each lead of the standard 12-lead ECG, and wherein the calculating step produces a residuum signal for each lead of the standard 12-lead ECG.

4. The method of claim 1, wherein the quantifying step quantifies an R-wave heterogeneity by calculating a maximum square root of a second central moment of the residuum signals about the averaged residuum signal occurring within a QRS duration.

5. The method of claim 1, wherein the quantifying step quantifies a T-wave heterogeneity by calculating a maximum square root of a second central moment of the residuum signals about the averaged residuum signal occurring within a JT interval.

6. The method of claim 1, wherein the quantifying step quantifies a P-wave heterogeneity by calculating a maximum square root of a second central moment of the residuum signals about the averaged residuum signal occurring within a PQ interval.

7. The method of claim 1, wherein the quantifying step quantifies an ST-segment heterogeneity by calculating a maximum square root of a second central moment of the residuum signals about the averaged residuum signal occurring within an ST interval.

8. The method of claim 2, further comprising identifying a peak level of at least one of quantified R-wave heterogeneity, T-wave heterogeneity, P-wave heterogeneity, and ST-segment heterogeneity.

9. The method of claim 8, further comprising determining a trend of at least one of peak R-wave heterogeneity level, peak T-wave heterogeneity level, peak P-wave heterogeneity level, and peak ST-segment heterogeneity level over a period of time.

10. The method of claim 8, wherein the step of identifying further comprises using the peak level to predict risk for cardiac arrhythmias.

11. The method of claim 1, wherein the generating step comprises computing a median-beat for each ECG signal of the first set of ECG signals.

12. The method of claim 11, wherein the median-beat is computed over a time period between 5 and 10 minutes.

13. An electrocardiogram (ECG) system for quantifying risk of cardiac arrhythmia, comprising:
   an input module configured to receive ECG signals from spatially separated leads; and
   a processor configured to:
      generate a baseline beat template associated with the morphology of each ECG signal of a first set of ECG signals from the spatially separated leads,
      calculate a difference between each ECG signal of a second set of ECG signals from the spatially separated leads and the corresponding baseline beat template to produce a residuum signal for each of the spatially separated leads,
      average the residuum signals across the leads to produce an averaged residuum signal; and
      quantify a spatio-temporal heterogeneity of the second set of ECG signals based on the residuum signals and the averaged residuum signal, wherein the spatio-temporal heterogeneity is associated with arrhythmia risk.

14. The system of claim 13, wherein the processor is configured to quantify R-wave heterogeneity, T-wave heterogeneity, P-wave heterogeneity, and ST-segment heterogeneity.

15. The method of claim 13, wherein the processor is configured to quantify at least one selected from the group consisting of R-wave heterogeneity, T-wave heterogeneity, P-wave heterogeneity, and ST-segment heterogeneity.

16. The system of claim 15, wherein the processor is configured to produce a residuum signal for each lead of a standard 12-lead ECG.

17. The system of claim 13, wherein the processor is further configured to quantify an R-wave heterogeneity by calculating a maximum square root of a second central moment of the averaged residuum signal occurring within a QRS duration.

18. The system of claim 13, wherein the processor is further configured to quantify a T-wave heterogeneity by calculating a maximum square root of a second central moment of the averaged residuum signal occurring within a JT interval.

19. The system of claim 13, wherein the processor is further configured to quantify a P-wave heterogeneity by calculating a maximum square root of a second central moment of the averaged residuum signal occurring within a PQ interval.

20. The system of claim 13, wherein the processor is further configured to quantify an ST-segment heterogeneity by calculating a maximum square root of a second central moment of the averaged residuum signal occurring within an ST interval.

21. The system of claim 13, wherein the processor is further configured to determine at least one of peak quantified R-wave heterogeneity, peak T-wave heterogeneity, peak P-wave heterogeneity, and peak ST-segment heterogeneity.

22. The system of claim 21, wherein the processor is further configured to determine a trend of at least one of the peak R-wave heterogeneity, peak T-wave heterogeneity, peak P-wave heterogeneity, and peak ST-segment heterogeneity levels over a period of time.

23. The system of claim 13, wherein the processor is further configured to compute a median-beat for each ECG signal of the first set of ECG signals to generate each baseline beat template.

24. The system of claim 23, wherein the median-beat is computed over a time period between 5 and 10 minutes.

25. A computer program product stored on non-transitory computer readable media, including a set of instructions that, when executed by a computing device, perform a method of quantifying risk of cardiac arrhythmia, comprising:
receiving a first set of electrocardiogram (ECG) signals;
generating a baseline measurement associated with the morphology of each ECG signal of the first set of ECG signals;
receiving a second set of ECG signals;
calculating, for each lead, a difference between each ECG signal in the second set of ECG signals and the corresponding baseline measurement to produce a residuum signal for each lead;
averaging the residuum signals across the leads to produce an averaged residuum signal; and
quantifying, a spatio-temporal heterogeneity of the second set of ECG signals based on the residuum signals and the averaged residuum signal, wherein the spatio-temporal heterogeneity is correlated with arrhythmia risk.

* * * * *